US009216554B2

(12) United States Patent
Muramatsu et al.

(10) Patent No.: US 9,216,554 B2
(45) Date of Patent: *Dec. 22, 2015

(54) PROCESS OF FUSION-BONDING PLASTIC FILM AND DRUG BAG

(71) Applicant: Ajinomoto Co., Inc., Chuo-ku (JP)

(72) Inventors: Yasuhiro Muramatsu, Shizuoka (JP); Kaoru Shimizu, Shizuoka (JP)

(73) Assignee: AJINOMOTO CO., INC., Chuo-ku (JP)

( * ) Notice: Subject to any disclaimer, the term of this patent is extended or adjusted under 35 U.S.C. 154(b) by 190 days.

This patent is subject to a terminal disclaimer.

(21) Appl. No.: 13/899,668

(22) Filed: May 22, 2013

(65) Prior Publication Data

US 2013/0259407 A1 Oct. 3, 2013

Related U.S. Application Data

(63) Continuation of application No. 12/706,381, filed on Feb. 16, 2010, now Pat. No. 8,469,938, which is a continuation of application No. PCT/JP2008/064638, filed on Aug. 15, 2008.

(30) Foreign Application Priority Data

Aug. 16, 2007 (JP) .................................. 2007-212136

(51) Int. Cl.
*B31B 1/64* (2006.01)
*B65D 30/00* (2006.01)
(Continued)

(52) U.S. Cl.
CPC ... *B31B 1/64* (2013.01); *A61J 1/10* (2013.01); *A61J 1/2093* (2013.01);
(Continued)

(58) Field of Classification Search
CPC ............. A61J 1/14; A61J 1/1412; A61J 1/10; A61J 1/1475; A61J 2001/202; A61J 2001/2024; A61J 1/2093; A61J 2200/42; B29C 65/1477; B29C 65/1612; B29C 65/1616; B29C 65/1619; B29C 65/1622; B29C 65/1635; B29C 65/1645; B29C 65/1654; B29C 65/1664; B29C 65/1677; B29C 65/168; B29C 65/1683; B29C 65/76; B29C 66/53263; B23K 26/206
See application file for complete search history.

(56) References Cited

U.S. PATENT DOCUMENTS 4,636,609 A 1/1987 Nakamata
4,847,462 A * 7/1989 Soodak et al. ........... 219/121.63
(Continued)

FOREIGN PATENT DOCUMENTS

JP 4-102580 A 4/1992
JP 4-157082 5/1992
(Continued)

OTHER PUBLICATIONS

JP2005-380409 translation Apr. 24, 2015.*
(Continued)

*Primary Examiner* — Adam Marcetich
(74) *Attorney, Agent, or Firm* — Oblon, McClelland, Maier & Neustadt, L.L.P.

(57) ABSTRACT

The present invention relates to a process of fusion-bonding a plastic film (8a, 8b) to an object to be fusion-bonded such as a port member (16) in manufacturing a drug bag, and relates to a drug bag. The present fusion-bonding process comprises steps of disposing a heat generation element generating heat by absorbing infrared laser, on an opposite surface (8c) of the plastic film (8a, 8b) from the port member (16), or between the port member (16) and the plastic film (8a, 8b), pressing a press member (30a, 30b), which allows infrared laser to be transmitted therethrough, from a side of the plastic film (8a, 8b), and irradiating the infrared laser (L) to the heat generation element (24a, 24b) through the press member (30a, 30b).

8 Claims, 11 Drawing Sheets

(51) Int. Cl.
*A61J 1/10* (2006.01)
*A61J 1/20* (2006.01)
*B29C 65/16* (2006.01)
*B65D 81/32* (2006.01)
*A61J 1/14* (2006.01)
*B29C 65/18* (2006.01)
*B29C 65/76* (2006.01)
*B29C 65/00* (2006.01)
*B29C 35/08* (2006.01)
*B29L 31/00* (2006.01)

(52) U.S. Cl.
CPC ........ *B29C 65/1612* (2013.01); *B29C 65/1616* (2013.01); *B29C 65/1629* (2013.01); *B29C 65/1635* (2013.01); *B29C 65/1645* (2013.01); *B29C 65/1683* (2013.01); *B29C 66/1122* (2013.01); *B29C 66/346* (2013.01); *B29C 66/3472* (2013.01); *B29C 66/472* (2013.01); *B29C 66/53263* (2013.01); *B29C 66/81267* (2013.01); *B29C 66/83221* (2013.01); *B65D 31/00* (2013.01); *B65D 81/3266* (2013.01); *A61J 1/1475* (2013.01); *A61J 2200/42* (2013.01); *A61J 2205/30* (2013.01); *A61M 2207/00* (2013.01); *B29C 65/168* (2013.01); *B29C 65/1654* (2013.01); *B29C 65/1664* (2013.01); *B29C 65/18* (2013.01); *B29C 65/76* (2013.01); *B29C 66/0242* (2013.01); *B29C 66/24* (2013.01); *B29C 66/43* (2013.01); *B29C 66/71* (2013.01); *B29C 66/7352* (2013.01); *B29C 66/919* (2013.01); *B29C 66/9161* (2013.01); *B29C 66/91411* (2013.01); *B29C 66/91933* (2013.01); *B29C 2035/0822* (2013.01); *B29L 2031/7148* (2013.01)

(56) References Cited

U.S. PATENT DOCUMENTS

| | | | |
|---|---|---|---|
| 4,945,203 A | 7/1990 | Soodak et al. | |
| 5,279,693 A | 1/1994 | Robinson et al. | |
| 5,893,959 A | 4/1999 | Muellich | |
| 6,103,050 A * | 8/2000 | Krueger | 156/251 |
| 6,132,780 A * | 10/2000 | Archibald et al. | 426/106 |
| 7,255,770 B2 | 8/2007 | Wissman | |
| 7,527,760 B2 | 5/2009 | Watanabe et al. | |
| 7,572,492 B2 | 8/2009 | Bager et al. | |
| 7,658,279 B2 | 2/2010 | Oka et al. | |
| 7,815,624 B2 | 10/2010 | Larson | |
| 7,820,936 B2 | 10/2010 | Weber et al. | |
| 7,862,874 B2 | 1/2011 | Asada et al. | |
| 7,935,095 B2 | 5/2011 | Bager et al. | |
| 8,469,938 B2 * | 6/2013 | Muramatsu et al. | 604/410 |
| 2003/0201059 A1 * | 10/2003 | Holman et al. | 156/155 |
| 2004/0030384 A1 | 2/2004 | Wissman | |
| 2004/0175522 A1 | 9/2004 | Tajima | |
| 2005/0087456 A1 | 4/2005 | Oka et al. | |
| 2005/0109452 A1 * | 5/2005 | Basque et al. | 156/251 |
| 2005/0186377 A1 | 8/2005 | Hurst et al. | |
| 2006/0194009 A1 | 8/2006 | Tajima | |
| 2007/0065659 A1 * | 3/2007 | Kihara et al. | 428/323 |
| 2007/0295445 A1 * | 12/2007 | Maatta et al. | 156/272.8 |
| 2011/0033133 A1 * | 2/2011 | Kujat | 383/20 |

FOREIGN PATENT DOCUMENTS

| | | | | |
|---|---|---|---|---|
| JP | 2003-159310 | | 6/2003 | |
| JP | 2003-181931 | | 7/2003 | |
| JP | 2004-500990 A | | 1/2004 | |
| JP | 2004-142225 | | 5/2004 | |
| JP | 2004-267384 | | 9/2004 | |
| JP | 2005187030 A | * | 7/2005 | B65D 77/08 |
| JP | 2007-39115 | | 2/2007 | |
| JP | 2007-175396 A | | 7/2007 | |
| JP | 2007-175442 | | 7/2007 | |
| WO | WO 02/00144 A1 | | 1/2002 | |
| WO | 2005-080067 | | 9/2005 | |
| WO | 2006/085659 | | 8/2006 | |

OTHER PUBLICATIONS

Office Action issued Feb. 2, 2015, in Japan Patent Application No. 2013-096495, filed May 1, 2013 (with partial English-language translation).

Office Action issued Aug. 18, 2014, in Japanese Patent Application No. 2013-096495 with English translation.

Office Action issued Mar. 12, 2012, in Japanese Patent Application No. 2009-528154.

Office Action issued Mar. 4, 2013, in Japanese Patent Application No. 2009-528154.

Translation in English of JP 2007-175442 Application Publication of date Dec. 7, 2007.

Extended European Search Report issued Feb. 6, 2014 in Patent Application No. 08827513 6.

* cited by examiner

US 9,216,554 B2

PROCESS OF FUSION-BONDING PLASTIC FILM AND DRUG BAG

CROSS-REFERENCE TO RELATED APPLICATIONS

The present application is a continuation of and claims the benefits of priority to U.S. application Ser. No. 12/706,381, filed Feb. 16, 2010, the entire content of which is incorporated herein by reference. U.S. application Ser. No. 12/706,381 is a continuation of PCT/JP08/064638, filed Aug. 15, 2008, and claims the benefits of priority to Japanese Application No. 2007-212136, filed Aug. 16, 2007.

FIELD OF THE INVENTION

The present invention relates to a process of fusion-bonding a plastic film, and specifically to a process of fusion-bonding a plastic film to be fusion-bonded to an object to be fusion-bonded by means of infrared laser in manufacturing a drug bag. Further, the present invention relates to a drug bag in which a plastic film to be fusion-bonded is fusion bonded to an object to be fusion-bonded.

BACKGROUND OF THE INVENTION

Conventionally, a drug bag containing a drug such as infusion solution for administering it to a patient is known.

FIG. 14 is a schematic exploded perspective view of a conventional typical drug bag. As shown in FIG. 14, a drug bag 200 has a drug bag body 202 with a compartment 201 containing a drug such as an infusion solution, and a plastic tubular port member 203 communicating the compartment 201 with the exterior of the drug bag 200 to discharge the drug. The port member 203 is normally closed by a rubber plug 204, but when the drug is administered to a patient, the port member 203 is opened by penetrating a hollow infusion needle through the rubber plug 204.

The drug bag body 202 is formed by fusion-bonding peripheral portions of two plastic films 205a, 205b to each other so as to form the compartment 201. Further, the port member 203 is sandwiched between the two plastic films 205a, 205b and fusion-bonded to the two plastic films 205a, 205b. These fusion-bonding processes are generally performed by means of a heat-sealing process explained below.

FIG. 15 is a view for explaining the fusion-bonding process at the peripheral portions of the two plastic films. As shown in FIG. 15, heated sealing molds 206 are disposed on the opposed sides of the two plastic films 205a, 205b (see FIG. 15(a)), the sealing molds 206 are pressed against the two plastic films 205a, 205b to melt the two plastic films 205a, 205b at the same time (see FIG. 15(b)), and the two plastic films 205a, 205b are fusion-bonded to each other (see FIG. 15(c)).

FIG. 16 is a view for explaining the fusion-bonding process between the two plastic films and the port member. As shown in FIG. 16, after the port member 203 is inserted between the two plastic films 205a, 205b, heated sealing molds 207 are disposed on the opposite sides of the two plastic films 205a, 205b (see FIG. 16(a)), the sealing molds 207 are pressed against the two plastic film 205a, 205b (see FIG. 16(b)), and the plastic films 205a, 205b and the port member 203 are fusion-bonded to each other (see FIG. 16(c)).

However, although the two plastic films 205a, 205b become a melted state by means of the sealing molds 207 right after the press action thereof, since the sealing molds 207 do not contact the port member 203, a surface of the port member 205 becomes a melted state later due to a heat conducted through the two plastic films 205a, 205b. Thus, while the surface of the port member 203 becomes the melted state, the two plastic films 205a, 205b become an excess melted state. As a result, although the two plastic films 205a, 205b and the port member 203 are fusion-bonded to each other, damage is caused around the fusion-bonded location 208 of the plastic films 205a, 205b, and concretely portion around the fusion-bonded location 208 are raised or become dirty (see FIG. 16(c)). Thus, by inserting the port member 203 between the two plastic films 205a, 205b after the port member 203 is preheated, the plastic films 205a, 205b and the port member 203 become the melted states at the same time so that the damage can be avoided (see FIG. 16(d)).

On the other hand, a technology is known of using a laser beam in the process of fusion-bonding the peripheral portions of the two plastic films 205a, 205b (please refer to the Patent Publication 1 indicated later). FIG. 17 is a view for explaining a fusion-bonding process disclosed in the Patent Publication 1. As shown in FIG. 17, a heat generating member 208 generating heat by absorbing a laser beam is disposed under the two plastic films 205a, 205b, the two plastic films 205a, 205b are pressed from an upper side thereof by a transparent holding member 209, the laser beam L is irradiated to the heat generating member 208 through the holding member 209 and the two plastic films 105a, 205b, and heat generated by the heat generating member 208 allows the two plastic films 205a, 205b to become a melted state and fusion-bond to each other.

[Patent Publication 1] Japanese Patent Laid-open Publication No. 2004-142225

DISCLOSURE OF THE PRESENT INVENTION

Problem to be Solved by the Present Invention

As stated above, when the two plastic films 205a, 205b are fusion-bonded to each other, the heat-sealing process or the laser beam process disclosed in the Patent Publication 1 can be used. However, in case the two plastic films 205a, 205b are fusion-bonded to the port member 203, when the heat-sealing process is employed, a step of previously heating the port member 203 is needed, and when the laser beam process disclosed in the Patent Publication 1 is employed, the port member 203 has to be made of a light transmitting material, and fusion bonding processes on the front and back sides cannot be performed at the same time.

Further, in a design technology of a mold for fusion-bonding the port member 203, since a melted amount of the port member is needed to be determined taking into consideration a thickness of the two plastic films and a shape and a material of the port member, the design of this mold is very difficult, and maintaining a stable fusion-bonding state is also difficult.

The present inventor tested to easily fusion-bonding the two plastic films to the port member or other objects to be fusion-bonded by adding an idea to the laser beam process.

Therefore, an object of the present invention is, in manufacturing a drug bag, to provide a process of easily fusion-bonding a plastic film to an object to be fusion-bonded by means of infrared laser. Further, another object of the present invention is to provide a drug bag in which a plastic film is fusion-bonded to an object to be fusion-bonded by means of infrared laser.

Means for Solving the Problem

To achieve the above-stated objects, in manufacturing a drug bag, a process of fusion-bonding an object to be fusion-bonded to a front-side plastic film of two front-side and back-side plastic films for a body of the drug bag sealed with each other to form a compartment containing a drug, comprises steps of disposing a heat generation element generating heat by absorbing infrared laser, on a front surface of the object or the front-side plastic film, or between the object and the front-side plastic film, pressing a press member, which allows infrared laser to be transmitted therethrough, against the front-side plastic film and the object from a front side of the drug bag, and irradiating the infrared laser to the heat generation element through the press member during the pressing step.

In this process, while the press member is pressed against the plastic film to be fusion-bonded and the object to be fusion-bonded, the infrared laser is irradiated to the heat generation element so that the heat generation element becomes a hot temperature instantaneously. This causes the surface of the plastic film for the drug bag body and the surface of the object around the heat generation element to become respective melted states so that the plastic film and the object are fusion-bonded to each other simply and cleanly.

In the fusion-bonding process according to the present invention, preferably, the object to be fusion-bonded is constituted of a plastic port member fusion-bonded between the two plastic films for the drug bag body for communicating the compartment with the exterior thereof.

In this fusion-bonding process, the heat generation element becomes a hot temperature instantaneously. This causes a surface of the plastic film for the drug bag body and a surface of the port member to become respective melted states at approximately the same time so that damage to the plastic film can be reduced more than the heat-sealing process.

Further, in the fusion-bonding process according to the present invention, preferably, the two plastic films for the drug bag body are sealed so as to form a plurality of the compartments containing drugs, the plurality of compartments are defined by a strong seal portion sealing a periphery of the drug bag and a weak seal portion serving as a partition between the compartments, and the object to be fusion-bonded is constituted of a plastic film for a handle fusion-bonded for opening the weak seal portion by pulling the handle.

In this fusion-bonding process, the heat generation element becomes a hot temperature instantaneously. This causes a surface of the plastic film for the handle and a surface of the plastic film for the drug bag body to become respective melted states at approximately the same time so that these plastic films can be fusion-bonded simply and cleanly.

In this fusion-bonding process, preferably, the drug bag has a port member for communicating one of the compartments with the exterior thereof, and the weak seal portion includes a first weak seal portion near the port member and a second weak seal portion far from the port member, and in the step of disposing the heat generation element, the heat generation element is disposed at equal distances from the first weak seal portion and the second weak seal portion or nearer the second weak seal portion than the first weak seal portion.

In this fusion-bonding process, when sealing strengths of the first weak seal portion and the second weak seal portion are equal to each other, an order of opening these weak seal portions can be controlled.

Further, in the above-stated fusion-bonding process, preferably, the two plastic films for the drug bag body allow infrared laser to be transmitted therethrough, the drug bag further comprises a plastic film for another handle fusion-bonded onto the back-side plastic film for the drug bag body for opening the weak seal portion by pulling the handles, in the step of disposing the heat generation element, a first heat generation element adjacent to the front-side plastic film for the handle and a second heat generation element adjacent to the back-side plastic film for the handle are arranged without overlapping each other, and in the step of irradiating the infrared laser, the infrared laser is irradiated from the front side of the drug bag through the press member, to the first heat generation element and through the two plastic films to the second heat generation element.

In this fusion-bonding process, the front-side and back-side plastic films for the handles can be fusion-bonded at the same time by means of an irradiation of the infrared laser only from the front side of the drug bag.

In this fusion-bonding process, preferably, the first heat generation elements and the second heat generation elements are alternately disposed in a line form.

Preferably, the infrared laser has a wavelength belonging to a wavelength band of 700-1200 nm.

Namely, the wavelength of the laser for fusion-bonding the object to the plastic film used in the drug bag is preferably longer than those of ultraviolet laser and visible laser. Thus, infrared laser having small energy is preferable, and a wavelength band thereof is preferably a range of 700-1200 nm.

Further, in the fusion-bonding process according to the present invention, the heat generation element may be defined by an ink applied to the plastic film or the object, a plastic film to which an ink absorbing infrared laser is applied, or a plastic label to which an ink absorbing infrared laser is applied and which can be adhesively attached to the plastic film or the object.

Further, to achieve the above-stated object, in manufacturing a drug bag, a process of fusion-bonding a plastic film to be fusion-bonded to an object to be fusion-bonded is provided, the process comprising steps of disposing a heat generation element generating heat by absorbing infrared laser, on an opposite surface of the plastic film from the object or between the object and the plastic film, pressing a press member, which allows infrared laser to be transmitted therethrough, against the plastic film and the object from a side of the plastic film, and irradiating the infrared laser to the heat generation element through the press member during the pressing step.

In this process, while the press member is pressed against the plastic film to be fusion-bonded and the object to be fusion-bonded from the side of the plastic-film, the infrared laser is irradiated to the heat generation element so that the heat generation element becomes a hot temperature instantaneously. This causes the plastic film and a surface of the object around the heat generation element to become respective melted states at approximately the same time so that the plastic film and the object are fusion-bonded simply and cleanly.

In the above-stated fusion-bonding process according to the present invention, preferably, the plastic film is constituted of two plastic films for a body of the drug bag sealed to each other so as to form a compartment containing a drug, and the object is constituted of a plastic port member sandwiched and fusion-bonded between the two plastic films for the drug bag body for communicating the compartment and the exterior thereof.

In this fusion-bonding process, the heat generation element becomes a hot temperature instantaneously. This causes the two plastic films for the drug bag body and a surface of the port member to become respective melted states at approximately the same time so that damage to the two plastic films can be reduced more than that in the heat-sealing process.

Further, in the above-stated fusion-bonding process according to the present invention, preferably, the drug bag has two plastic films for a body of the drug bag body sealed to each other so as to form a plurality of compartments containing drugs, the plurality of compartments are defined by a strong seal portion sealing a periphery of the drug bag and a weak seal portion serving as a partition between the compartments, and the plastic film to be fusion-bonded is constituted of a plastic film for a handle fusion-bonded to the plastic film for the drug bag body for opening the weak seal portion by pulling the handle.

In this fusion-bonding process, the heat generation element becomes a hot temperature instantaneously. This causes both of the plastic film for the handle and the plastic film for the drug bag body to become respective melted states at approximately the same time so that both of the plastic films are fusion-bonded to each other simply and cleanly.

Further, to achieve the above-stated object, a drug bag according to the present invention comprises two plastic films for a body of the drug bag sealed to each other so as to form a compartment containing a drug; a plastic port member sandwiched and fusion-bonded between the two plastic films for the drug bag body for communicating the compartment and the exterior thereof; and a heat generation element generating heat by absorbing infrared laser and disposed at a location where the port member is fusion-bonded.

Further, to achieve the above-stated object, a drug bag according to the present invention comprises; two plastic films for a body of the drug bag sealed to each other so as to form a plurality of compartments containing drugs, the plurality of compartments being defined by a strong seal portion sealing a periphery of the drug bag, and a weak seal portion serving as a partition between the compartments; plastic films for handles fusion-bonded to the respective two plastic films for the drug bag body for opening the weak seal portion by pulling the handles, and heat generation elements generating heat by absorbing infrared laser and disposed at locations where the plastic films for the handles are fusion-bonded.

Effect of the Present Invention

As stated above, the fusion-bonding process according to the present invention, in manufacturing a drug bag, allows a plastic film to be simply fusion-bonded to an object to be fusion-bonded by means of infrared laser. Further, a drug bag is provided, in which plastic films are fusion-bonded to an object to be fusion bonded by means of infrared laser.

DETAILED DESCRIPTION OF THE PREFERRED EMBODIMENTS

Firstly, referring to FIGS. 1-3, a first embodiment of a drug bag according to the present invention will be explained. FIG. 1 is a front view of a first-embodiment drug bag, FIG. 2 is a cross-sectional view taken along a line II-II shown in FIG. 1, and FIG. 3 is a cross-sectional view taken along a line III-III shown in FIG. 1.

As shown in FIGS. 1-3, a drug bag 1 has a rectangular bag body 2 extending in a longitudinal direction A in a substantially flat form, and the bag body 2 is formed by two plastic films, namely, a front-side plastic film 8a and a back-side plastic film 8b, sealed with each other so as to form two compartments 4, 6 containing drugs. A material of the two plastic films 8a, 8b is, for example, polyethylene or polypropylene commonly used for medical applications. A thickness of the two plastic films 8a, 8b is, for example, 250 micrometers. When the drug bag 1 is reversed, components on the front side correspond to those on the back side, and vice versa.

The two compartments 4, 6 are defined by a strong seal portion 10 sealing periphery of the drug bag body 2 and a weak seal portion 12 serving as a partition between the compartments 4, 6. Specifically, the periphery of the bag body 2 is pressed and sealed at a temperature sufficiently higher than a melting temperature of the two plastic films 8a, 8b (for example, 145° C. in case of polyethylene) so as to form the strong seal portion 10 and a cavity inside thereof. Further, an intermediate portion of the bag body 2 in the longitudinal direction A is pressed and sealed at a temperature a little higher than the melting temperature of the two plastic films 8a, 8b (for example, 120° C. in case of polyethylene) so as to form the weak seal portion 12 across the bag body 2 in a width direction B. The inside cavity of the bag body 2 is defined by the strong seal portion 10 and partitioned into the first compartment 4 and the second compartment 6 by and the weak seal portion 12. Different kinds of drugs (not shown) are sealingly enclosed in the first and second compartments 4, 6. As explained later, a sealing strength of the strong seal portion 10 is larger than that of the weak seal portion 12 so that only the weak seal portion 12 can be opened to mix the drug in the first compartment 4 with the drug in the second compartment 6.

Further, the strong seal portion 10 has a hanging aperture 14 on a side of the second compartment 6 for hanging the drug bag 1, for example, from an infusion stand.

The drug bag 1 further has a port member 16 sandwiched and fusion-bonded between the two plastic films 8a, 8b to communicate the first compartment 4 with the exterior of the drag bag 1. The port member 16 has a tubular member 16a extending from the first compartment 4 through the two plastic films 8a, 8b to the exterior of the bag body 2, and a cap member 16b adhered to the tubular member 16a on the opposite side thereof from the bag body 2, the port member 16 defining a discharge aperture 18 for discharging the drugs in the first and second compartments 4, 6. Preferably, a cross-sectional profile of the tubular member 16a smoothly spreads in the width direction B. The tubular member 16a is preferably made of a plastic material compatible with the material of the drug bag 1, for example, polyethylene. The cap member 16b has an opening 16c forming an end of the discharge aperture 18, and annular periphery 16d disposed around the opening 16c. Further, the drug bag 1 has a rubber plug 20 sandwiched between the tubular member 16a and the cap member 16b to plug the discharge aperture 18. The opening 16c of the cap member 16b allows the plug 20 to be exposed, and when the drugs in the drug bag 1 is administered, an infusion needle contained in a drug set can be penetrated through the plug 20. The port member 16 is fusion-bonded to the two plastic films 8a, 8b at a sealing strength substantially equal to that of the strong seal portion 10.

The drug bag 1 further has plastic films 22a, 22b for handles respectively fusion-bonded to the two plastic films 8a, 8b for opening the weak seal portion 12 by pulling the handles. In the present embodiment, the plastic films 22a, 22b for the handles are fusion-bonded to film portions forming the first compartment 4 and placed close to the weak seal portion 12.

The weak seal portion 12 has a strength to a mere extent that, when the plastic films 22a, 22b for the handles are pulled away from each other, at least a portion of the weak seal portion 12 is separated to communicate the first compartment 4 with the second compartment 6. On the other hand, the strong seal portion 10 has a strength to an extent that, when the plastic films 22a, 22b for the handles are pulled away from each other, the strong seal portion 10 is maintained to be sealed. The plastic films 22a, 22b of the handles are fusion-bonded to the two plastic films 8a, 8b for the bag body at a sealing strength substantially equal to that of the strong seal portion 10, while the two plastic films 8a, 8b are fusion-bonded to the port member 16 at a sealing strength substantially equal to that of the strong seal portion 10.

Further, the drug bag 1 has heat generation elements 24a, 24b absorbing infrared laser to generating heat and disposed on portions of the plastic films where the port member is fusion-bonded and, other heat generation elements 26a, 26b absorbing infrared laser to generating heat and disposed at locations where the plastic films 22a, 22b for the handles are fusion-bonded. Each of the heat generation elements 24a, 24b, 26a, 26b may be an ink applied or printed onto the two plastic films 8a, 8b for the bag body or the plastic films 22a, 22b for the handles, a plastic film onto which an ink absorbing infrared laser is applied or printed, or a plastic label onto which an ink absorbing infrared laser is applied or printed and which can be adhesively attached to the plastic films 8a, 8b, 22a, 22b. The ink is arbitrary so long as it includes a color element which absorbs the laser, and is preferably a black ink. In this embodiment, the heat generation elements 24a, 24b, 26a, 26b are plastic black labels adhesively attached to front surfaces of the front-side plastic films 8a, 22a and back surfaces of the back-side plastic films 8b, 22b (namely, opposite surfaces from the first and second compartments 4, 6).

Next, referring to FIGS. 4 and 5, a manufacturing process of the drug bag 1 will be explained. FIG. 4 is a view for explaining a process of fusion-bonding the two plastic films for the bag body to the port member and FIG. 5 is a view for explaining a process of fusion-bonding the plastic films for the handles to the two plastic films for the bag body.

Firstly, the two plastic films 8a, 8b are prepared, and the strong seal portion 10 and the weak seal portion 12 are formed in the heat-sealing process (see FIG. 15). However, the strong seal portion 10 is not formed at opening locations through which the port member 16 is attached and through which drugs are injected into the first compartment 4 and the second compartment 6.

Next, the port member 16 incorporating the plug 20 is fusion-bonded to the two plastic films 8a, 8b. This fusion-bonding process is an example of the fusion-bonding process according to the present invention. Specifically, firstly, plastic labels defining the heat generation elements 24a, 24b are disposed and stuck onto a surface of the plastic films 8a, 8b on the opposite side thereof from the port member 16, namely, a front surface of the front-side plastic film 8a and a back surface 8c of the back-side plastic film 8b. The plastic labels 24a, 24b has respective sizes enough to seal the opening location to which the port member 16 is attached. Then, the port member 16 is inserted and positioned into the opening location of the plastic films 8a, 8b. Then, as shown in FIG. 4, press members 30a, 30b allowing infrared laser to be transmitted therethrough are pressed against the two plastic films 8a, 8b and the port member 16 from sides of the two plastic films 8a, 8b, namely, from the front and back sides of the drug bag. A pressing operation by means of the press members 30a, 30b is preferably performed from both of the front and back sides of the drug bag at the same time. The press members 30a, 30b are preferably made of a material which does not absorb a laser beam, such as glass and silicone rubber. The silicone rubber is preferable, because the silicone rubber can be deformed according to shapes of the plastic films 8a, 8b and the port member 16 when it is pressed thereagainst so that highly dimensional precision is not necessary. Then, while the press members 30a, 30b are pressed against the plastic films 8a, 8b and the port member 16, infrared laser L is irradiated through the press members 30a, 30b to the heat generation elements 24a, 24b.

When the infrared laser L is irradiated, the infrared laser L transmits through the press members 30a, 30b, reaches the heat generation elements 24a, 24b, and is absorbed by the heat generation elements 24a, 24b. This causes the heat generation elements 24a, 24b to generate heat and become a hot temperature instantaneously sufficient to melt the plastic films 8a, 8b and the surface of the port member 16. The heat of the heat generation elements 24a, 24b is transmitted to the plastic films 8a, 8b and the surface of the port member 16 so that they are melted and fusion-bonded to each other at approximately the same time. Thus, without preheating the port member 16, a clean seal reducing damage to the plastic films 8a, 8b can be formed.

Next, the plastic films 22a, 22b for the handles are fusion-bonded to the two plastic films 8a, 8b for the bag body. This fusion-bonding process is an example of the fusion-bonding process according to the present invention. Specifically, firstly, plastic labels which are the heat generation elements 26a, 26b are disposed between the plastic films 22a, 22b for the handles and the plastic films 8a, 8b for the bag body. Concretely, the plastic labels 26a, 26b are adhesively attached to the two plastic films 8a, 8b for the bag body, and the plastic films 22a, 22b for the handles are arranged outside of the two plastic films 8a, 8b. Then, as shown in FIG. 5, the press members 32a, 32b allowing the infrared laser to be transmitted therethrough are pressed against the plastic films 22a, 22b for the handles and the plastic films 8a, 8b for the bag body from the sides of the plastic films 22a, 22b for the handles, namely, from the front and back sides of the drug bag. As described above, the press members 32a, 32b are preferably made of a material which does not absorb the laser beam, for example, glass and silicone rubber. The silicone rubber is preferable, because the silicone rubber can be deformed according to shapes of the plastic films 8a, 8b and the port member 16 when it is pressed thereagainst so that highly dimensional precision is not necessary. Then, while the press members 32a, 32b are pressed against the plastic films 22a, 22b for the handles and the plastic films 8a, 8b for the bag body, infrared laser L is irradiated through the press members 32a, 32b to the heat generation elements 26a, 26b.

When the infrared laser L is irradiated, the infrared laser L transmits through the press members 32a, 32b and the plastic films 22a, 22b for the handles, reach the heat generation elements 26a, 26b, and is then absorbed by the heat generation elements 26a, 26b. This causes the heat generation elements 26a, 26b to generate heat and instantaneously become a hot temperature to sufficiently melt the surfaces of the two plastic films 8a, 8b for the bag body and the plastic films 22a, 22b for the handles opposing to each other. Since these surfaces are melted and then fusion-bonded to each other at approximately the same time, clean seals can be formed. An output of the infrared laser is adjusted so that the two plastic films 8a, 8b contacting each other are not fusion-bonded to each other. If the heat-sealing process or the laser beam process described in the Patent Publication 1 were employed, the two plastic films 8a, 8b would be fusion-bonded to each other, and thus it would be necessary for the plastic films 22a, 22b for the handles to be fusion-bonded to the two plastic films 8a, 8b for the bag body before the strong seal portion 10 and the weak seal portion 12 of the two plastic films 8a, 8b are formed. The fusion-bonding process according to the present invention therefore allows a fusion-bonding operation which cannot be achieved by means of the heat-sealing process and the laser beam process described in the Patent Publication 1.

An infrared laser irradiation apparatus is preferably a type of irradiating a plurality of irradiated locations arranged in a line form. A shape of the irradiated location or a shape of the irradiating light is any shape which can be represented by a light, and is, for example, circular, rectangular or oval. The shape of the irradiating light becomes a shape of a fusion-bonded location. A pitch of the irradiated locations is determined so that the irradiated locations overlap each other. When the irradiated locations are arranged so as to overlap each other, a continuous seal can be formed at once. An irradiating direction of the infrared laser toward the heat generation elements 24a, 24b is preferably a direction perpendicular to the surface of the heat generation elements 24a, 24b, but it may be obliged from the perpendicular direction so long as the fusion-bonding process can be performed. In this embodiment, since the cross-sectional profile of the tubular member 16a smoothly spreads in the width direction B, even if the irradiating directions of the infrared lasers toward the plurality of the irradiated locations in the heat generation elements 24a, 24b are parallel to each other, sufficient heat generation could be obtained.

The infrared laser irradiating apparatus is, for example, a semiconductor laser apparatus, a wavelength band of which is a range of 700-1200 nm. Since the wavelength of the infrared laser is longer than that of ultraviolet laser and visible laser and energy of the infrared laser is smaller than that of the ultraviolet and visible lasers, the infrared laser is suitable for being controlled so that only desirable locations of the thin two plastic films for the drug bag body are fusion-bonded to each other. Thus, unnecessary fusion-bonding operation caused in a direction different from the irradiating direction of the infrared laser can be easily prevented. Further, an output and time of irradiation are arbitrarily selected depending on a surface area (a fusion-bonded region) of an irradiated location. When a shape of one infrared laser at an irradiated location is circular and a diameter thereof is 2-10 mm, preferably, 3-7 mm, the output and time of irradiation are respectively, for example, 15-50 W and 1-5 seconds.

Instead of using the plastic label type of the heat generation elements 24a, 24b, 26a, 26b, the heat generation elements 24a, 24b, 26a, 26b may be printed onto the plastic films 8a, 8b. This allows a step of adhesively attaching the plastic label type of the heat generation elements 24a, 24b, 26a, 26b to be omitted. In this case, it is preferable to prevent positions of the heat generation elements 4a, 24b, 26a, 26b with respect to the strong seal portion 10 and the weak seal portion 12 from being shifted. Further, instead of using the plastic label type of the heat generation elements 24a, 24b, 26a, 26b, the plastic film type of the heat generation elements 24a, 24b, 26a, 26b may be used. This allows a material cost of the heat generation elements 24a, 24b, 26a, 26b to be reduced. In this case, when the plastic film type of the heat generation elements 24a, 24b, 26a, 26b are disposed, they are preferably held.

Finally, through the opening locations for injecting the drugs, the drugs are injected, and then the opening locations are sealed by means of the heat-sealing process.

Next, a process of using the drug bag will be explained.

The plastic films 22a, 22b for the handles are held by hands and pulled away from each other so that the weak seal portion 12 is opened. Then, the drug in the first compartment and the drug in the second compartment are mixed with each other sufficiently. The drug bag 1 is hanged from, for example, a stand by using the hanging aperture 14, and an infusion needle is penetrated through the plug 20 so that the mixed drugs are administered through the needle to a patient.

Then, referring to FIGS. 6-13, second to eighth embodiments of the drug bag according to the present invention will be explained. In FIGS. 6-13, components similar to those in the first embodiment are indicated by the same reference numbers as those in the first embodiment and explanations of the former components are omitted.

FIG. 6 is a front view of a second embodiment of the drug bag according to the present invention. As shown in FIG. 6, in the second-embodiment drug bag 40, the weak seal portion 12 includes a first weak seal portion 12a near the port member 16 and a second weak seal portion 12b far from the port member 16, the first compartment 4 is formed between the first weak seal portion 12a and the second weak seal portion 12b, and a third compartment 42 is formed between the first weak seal portion 12a and the port member 16. No drug is contained in the third compartment 42. Further, the heat generation elements 26a, 26b are disposed at equal distances from the first weak seal portion 12a and the second weak seal portion 12b.

The plastic films 22a, 22b for the handles are held by hands and pulled away from each other so that the weak seal portions 12a, 12b are opened. Since the heat generation elements 26a, 26b are disposed at the equal distances from the first weak seal portion 12a and the second weak seal portion 12b, the weak seal portions 12a, 12b are opened at approximate the same time. When the weak seal portions 12a, 12b are not opened, even if an infusion needle is penetrated through the plug 20, the drugs could not flow out of the drug bag 40. Only after the weak seal portions 12a, 12b are opened, the drugs are allowed to flow out of the drug bag 40. Thus, the drug in the first compartment 4 and the drug in the second compartment 6 are prevented from being administered to a patient without mixing these drugs with each other.

FIG. 7 is a front view of a third embodiment of the drug bag according to the present invention. As shown in FIG. 7, in the third-embodiment drug bag 50, the weak seal portion 12 includes a first weak seal portion 12a near the port member 16 and a second weak seal portion 12b far from the port member 16, the first compartment 4 is formed between the first weak seal portion 12a and the second weak seal portion, and a third compartment 52 is formed between the first weak seal portion 12a and the port member 16. No drug is contained in the third compartment 52. Further, the heat generation elements 26a, 26b are disposed nearer the second weak seal portion 12b than the first weak seal portion 12a.

The plastic films 22a, 22b for the handles are held by hands and pulled away from each other so that the weak seal portions 12a, 12b are opened. Since the heat generation elements 26a, 26b are disposed nearer the second weak seal portion 12b than the first weak seal portion 12a, the first weak seal portion 12a is opened after the second weak seal portion 12b is opened. When the weak seal portions 12a, 12b are not opened, even if an infusion needle is penetrated through the plug 20, the drugs could not flow out of the drug bag 50. Only after the weak seal portions 12a, 12b are opened, the drugs are allowed to flow out of the drug bag 50. Thus, the drug in the first compartment 4 and the drug in the second compartment 6 are prevented from being administered to a patient without mixing these drugs with each other. Further, it is preferable that only the second weak seal portion 12b is firstly opened to mix the drugs in the first and second compartments with each other, and then the first weak seal portion 12a is opened. In this case, the drug in the first compartment 4 and the drug in the second compartment 6 are surely prevented from being administered to a patient without mixing these drugs with each other. Conventionally, a drug bag is known in which an order of opening the first weak seal portion 12a and the second weak seal portion 12b is controlled by making a sealing strength of the first weak seal portion 12a stronger than that of the second weak seal portion 12b. In this case, a process of forming the first weak seal portion 12a is separated from a process of forming the second weak seal portion 12b. In the present embodiment, since such an order of opening the first and second weak seal portions 12a, 12b can be controlled by using the first weak seal portion 12a and the second weak seal portion 12b having the same sealing strength as each other, the first weak seal portion 12a and the second weak seal portion 12b can be formed in one process.

FIG. 8 is a front view of a fourth embodiment of the drug bag according to the present invention, and FIG. 9 is a view for explaining a process of fusion-bonding plastic films for the handles to the two plastic films for the bag body in the drug bag shown in FIG. 8. As shown in FIGS. 8 and 9, in the fourth-embodiment drug bag 60, the two plastic films 8a, 8b are made of a material allowing infrared laser to be transmitted therethrough, and a heat generation element 26a disposed on the front-side plastic film 8a and a heat generation element 26b disposed on the back-side plastic film 8b are arranged so as not to overlap each other when they are seen in an irradiating direction. Concretely, the front-side heat generation element 26a is arranged on a side of the weak seal portion 12 toward the first compartment 4 and the back-side heat generation element 26b is arranged on the other side thereof toward the second compartment 6 so that when the plastic films 22a, 22b for the handles are pulled away from each other, a force for opening the weak seal portion 12 is effectively applied to the weak seal portion 12.

As shown in FIG. 9, the plastic films 22a, 22b for the handles can be fusion-bonded to the two plastic films 8a, 8b for the bag body by irradiating the infrared laser from one side of the drug bag, namely, not from the opposite sides thereof, through a press member 32a to the front side heat generation element 26a and through the two plastic films 8a, 8b for the bag body to the back-side heat generation element 26b. The above-stated fusion-bonding process is preferably used in fifth to eighth embodiments of the drug bag described below.

FIG. 10 is a front view of a fifth embodiment of the drug bag according to the present invention. As shown in FIG. 10, the fifth-embodiment drug bag 70 can be obtained by modifying the positions of the heat generation elements 26a, 26b in the fourth-embodiment drug bag 60 onto the same side of the weak seal portion 12. The weak seal portion 12 may be opened in this arrangement.

FIG. 11 is a front view of a sixth embodiment of the drug bag according to the present invention. As shown in FIG. 11, in the sixth-embodiment drug bag 80, a plurality of the front-side heat generation element 26a and a plurality of the back-side heat generation elements 26b are alternately arranged in a line form.

Similar to the fourth embodiment drug bag 60, the plastic films 22a, 22b for the handles can be fusion-bonded to the two plastic films 8a, 8b for the bag body by irradiating the infrared laser L from one side of the drug bag.

FIG. 12 is a front view of a seventh embodiment of the drug bag according to the present invention. As shown in FIG. 12, in the seventh-embodiment drug bag 90, there are two weak seal portions 12 disposed on the opposite sides of the port member 16 in the longitudinal direction A, a first compartment 4a is formed by a first weak seal portion 12c, a second compartment 6a is formed by a second weak seal portion 12d, and a third compartment 92a is formed between the first weak seal portion 12c and the second weak seal portion 12d. No drug is contained in the third compartment 92a. Further, in a portion of the plastic film forming the third compartment 92, a plurality the front-side heat generation element 26a and a plurality of the back-side heat generation elements 26b are alternately arranged in a line form. Positions of the heat generation elements 26a, 26b are preferably determined so that when the plastic films 22a, 22b for the handles are pulled away from each other, the weak seal portion 12c, 12d are opened at approximately the same time.

Similar to the fourth embodiment drug bag 60, the plastic films 22a, 22b for the handles can be fusion-bonded to the two plastic films 8a, 8b for the bag body by irradiating the infrared laser L from one side of the drug bag. Further, when the weak seal portion 12c, 12d is not opened, even if an infusion needle is penetrated through the plug 20, the drugs could not flow out of the drug bag 90. Only after the weak seal portion 12c, 12d is opened, the drugs are allowed to flow out of the drug bag 90. Thus, the drug in the first compartment 4a and the drug in the second compartment 6a, the drugs are prevented from being administered to a patient without mixing these drugs with each other.

FIG. 13 is a front view of an eighth embodiment of the drug bag according to the present invention. As shown in FIG. 13, in the eighth-embodiment drug bag 10, three compartments 102a, 102b, 102c are formed by combining a first weak seal portion 12e extending in the longitudinal direction A with a second weak seal portion 12f extending in the width direction. Further, a plurality of the front-side heat generation element 26a and a plurality of the back-side heat generation elements 26b are alternately arranged in a line form. Positions of the heat generation elements 26a, 26b are preferably determined so that when the plastic films 22a, 22b for the handles are pulled away from each other, the weak seal portions 12e, 12f are opened at approximately the same time.

Similar to the fourth-embodiment drug bag 60, the plastic films 22a, 22b for the handles can be fusion-bonded to the two plastic films 8a, 8b for the bag body by irradiating the infrared laser L from one side of the drug bag.

Although the embodiments according to the present invention have been explained above, the present invention is not limited to these embodiments and allows various modifications within the scope of the claims, namely, such modifications fall within the scope of the present invention.

Although in the above-stated embodiments, the plastic labels or the heat generation elements 24a, 24b are disposed on the opposite surfaces of the two plastic films 8a, 8b from the port member 16, namely, on the front surface of the front-side plastic film 8a and the back surface 8c of the back-side plastic film 8b, the heat generation elements 24a, 24b may be disposed between the port member 16 and the two plastic films 8a, 8b. In this case, it is necessary to pay attention to prevent the heat generation elements 24a, 24b from being mixed into the drug. Further, although in the above-stated embodiments, the heat generation elements 26a, 26b are disposed between the plastic films 22a, 22b for the handles and the two plastic films 8a, 8b for the bag body, the heat generation elements 26a, 26b may be disposed on the opposite surfaces of the plastic films 22a, 22b for the handles from the two plastic films 8a, 8b for the bag body, namely, on the front surface of the front-side plastic film 22a and the back surface of the back-side plastic film 22b.

In the above-stated embodiments, the cross-sectional profile of the port member 16 may be circular. In this case, irradiating directions of the infrared lasers is preferably arranged closer to directions perpendicular to the cross-sectional profile.

In the above-stated embodiments, the infrared laser irradiation apparatus may be a type of irradiating one location. In this case, it is preferable that the infrared laser itself is scanned or the object to be irradiated (drug bag) may be scanned while the infrared laser is secured.

Although, in the above-stated embodiments, the object to be fusion-bonded to the plastic films 8a, 8b for the bag body is a port member 16 or the plastic films 22a, 22b for the handles, another object may be fusion-bonded to the plastic films 8a, 8b for the bag body.

Figure 1:
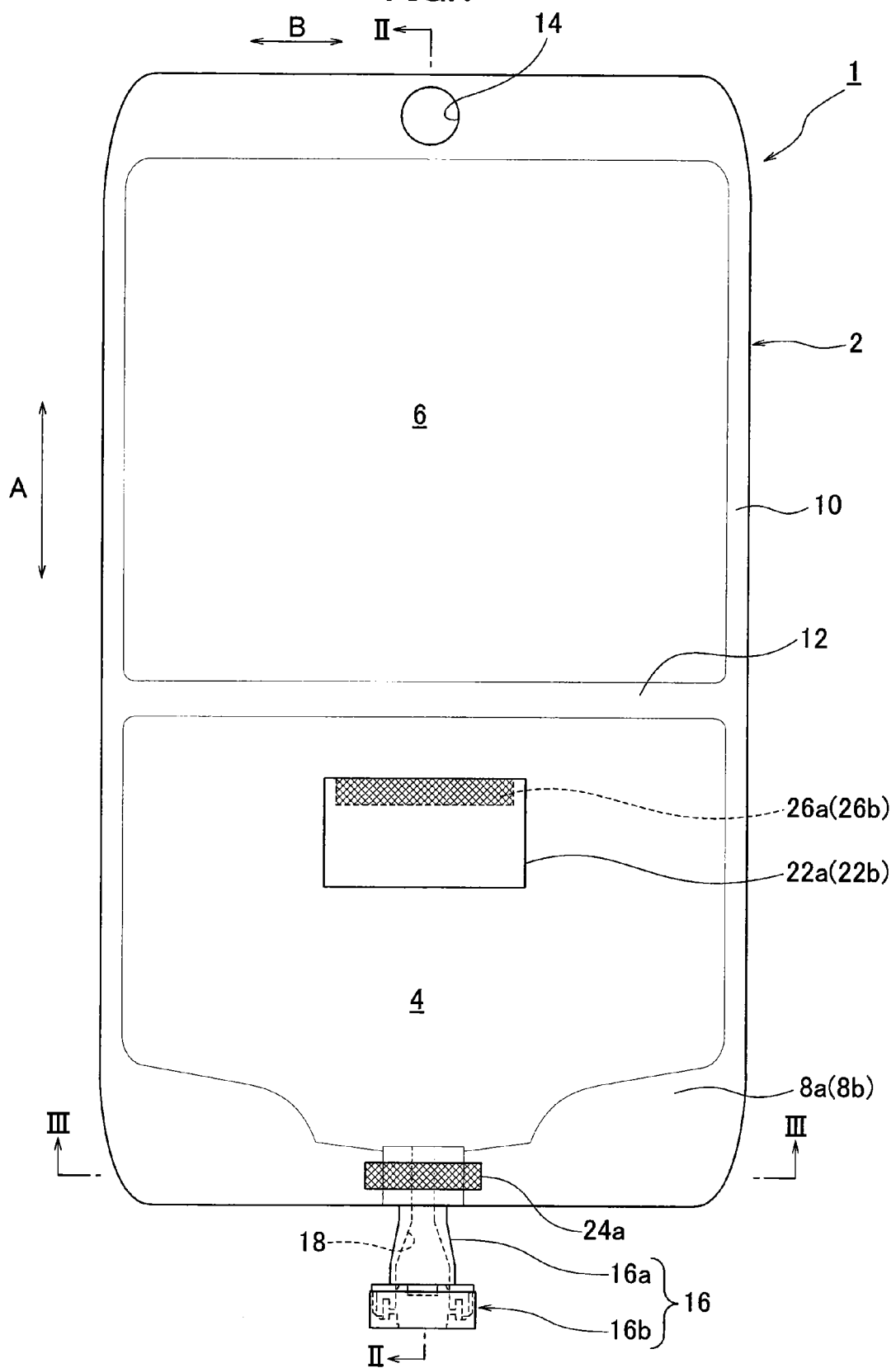
FIG. 1 is a front view of a first-embodiment drug bag according to the present invention.
Figure 2:
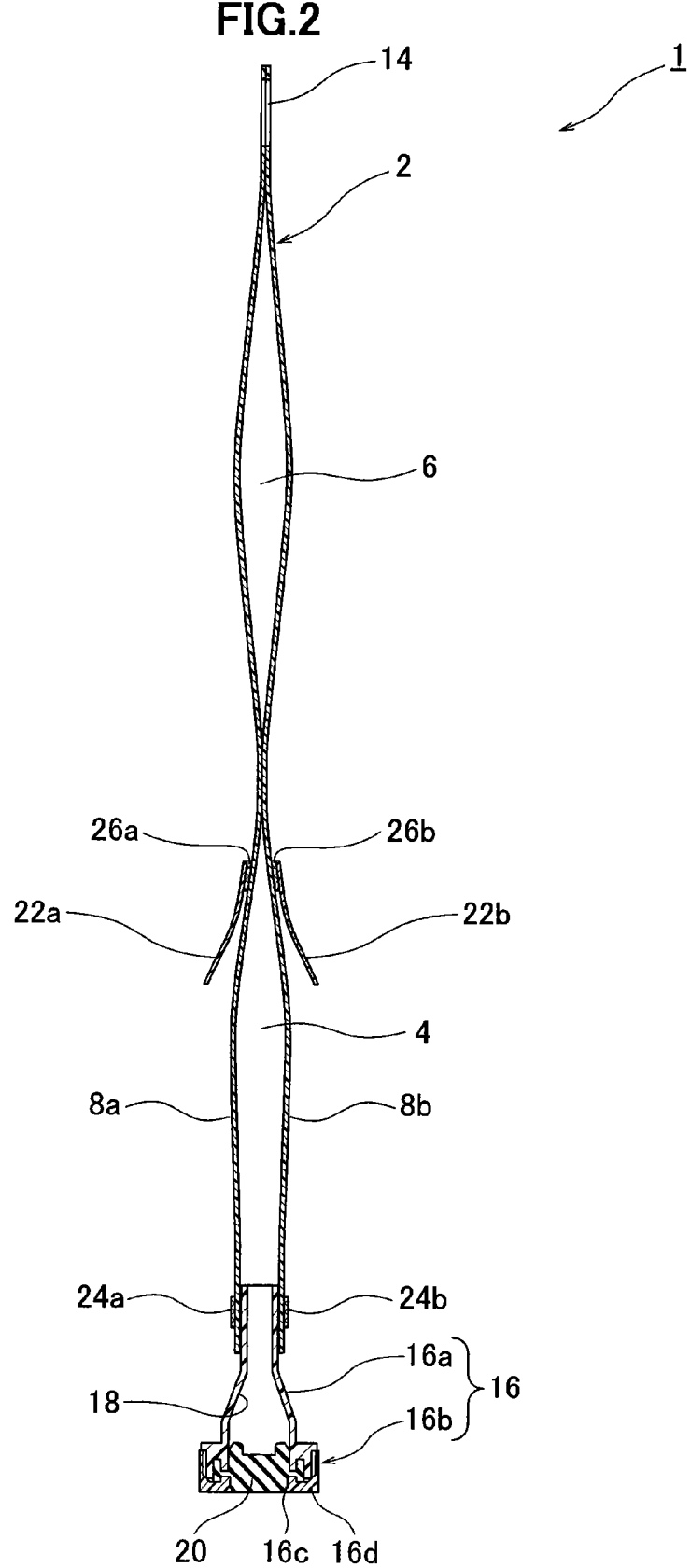
FIG. 2 is a cross-sectional view taken along the line II-II in FIG. 1.
Figure 3:
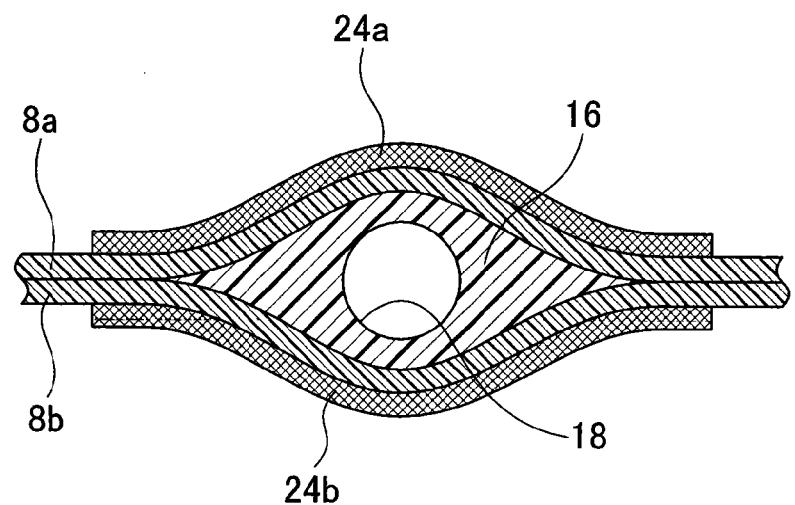
FIG. 3 is a cross-sectional view taken along the line III-III in FIG. 1.
Figure 4:
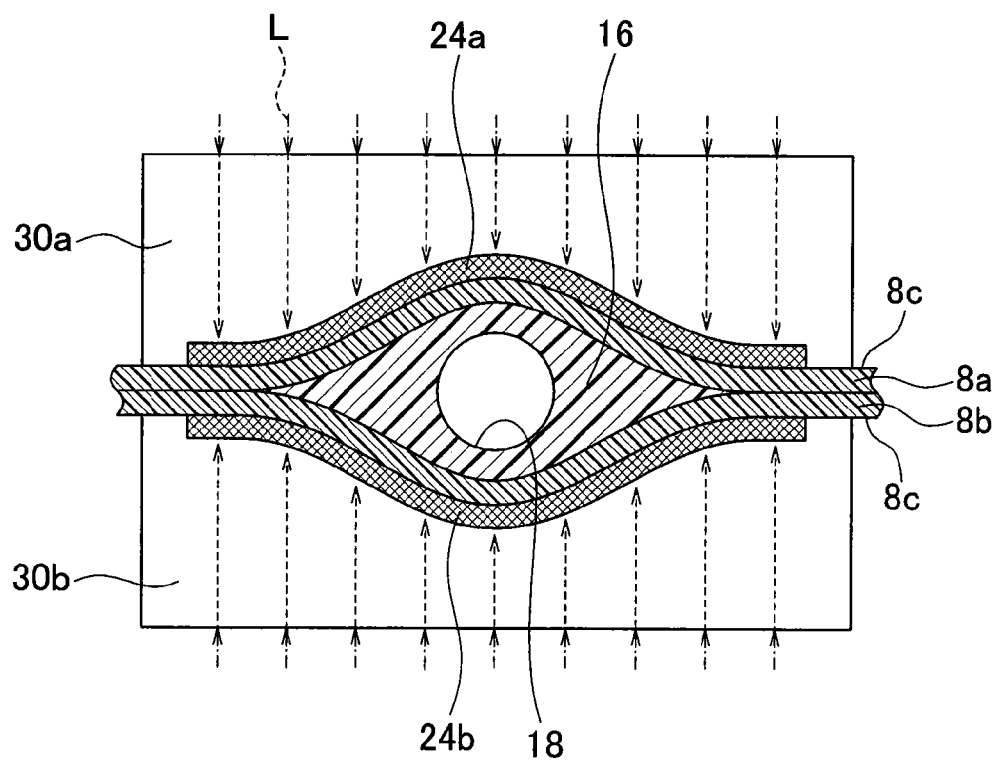
FIG. 4 is a view for explaining a process of fusion-bonding plastic films for a bag body to a port member.
Figure 5:
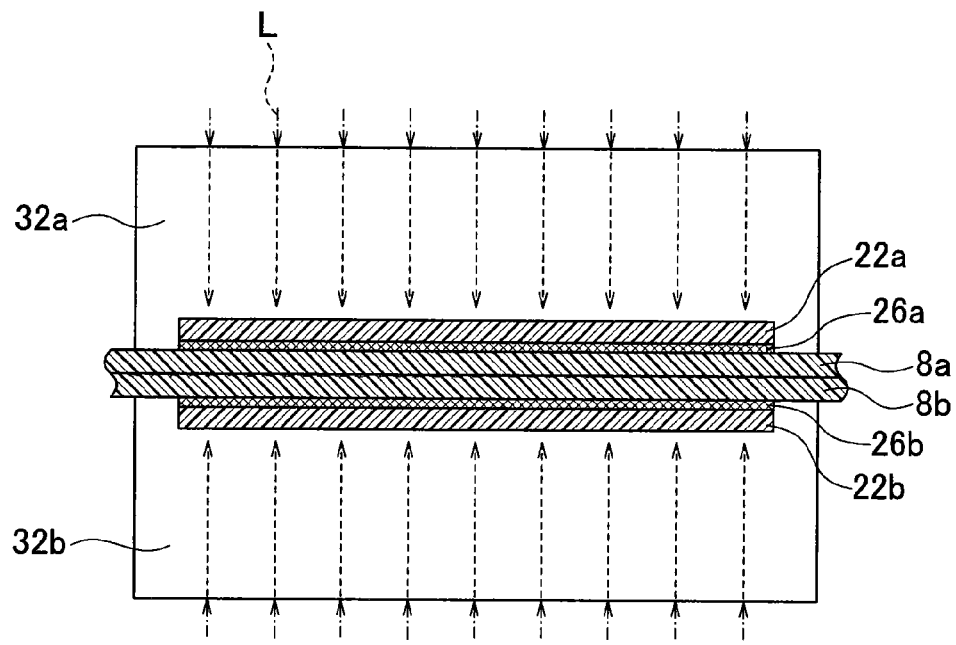
FIG. 5 is a view for explaining a process of fusion-bonding plastic films for handles to the plastic films for the bag body.
Figure 6:
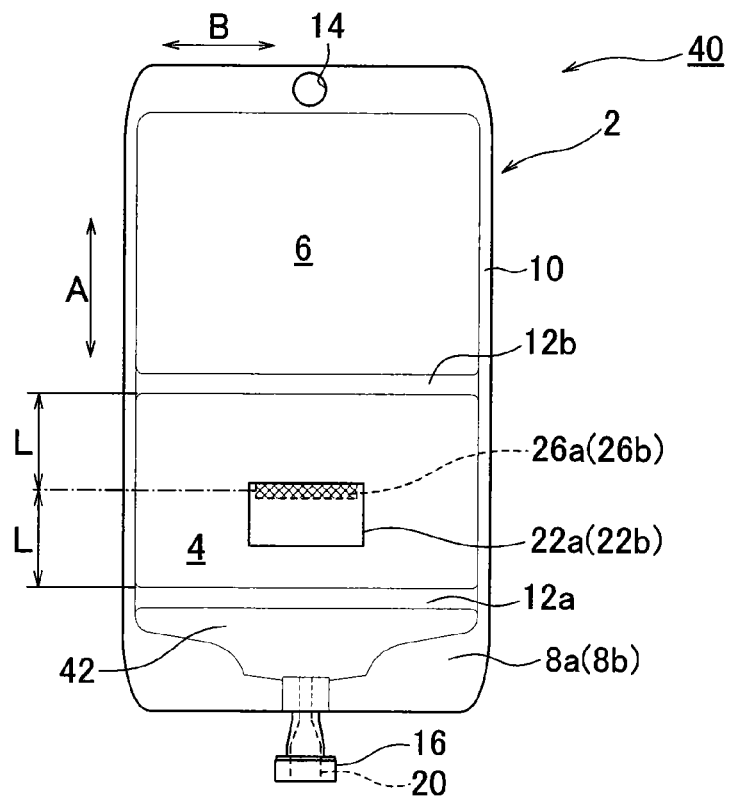
FIG. 6 is a front view of a second-embodiment drug bag according to the present invention.
Figure 7:
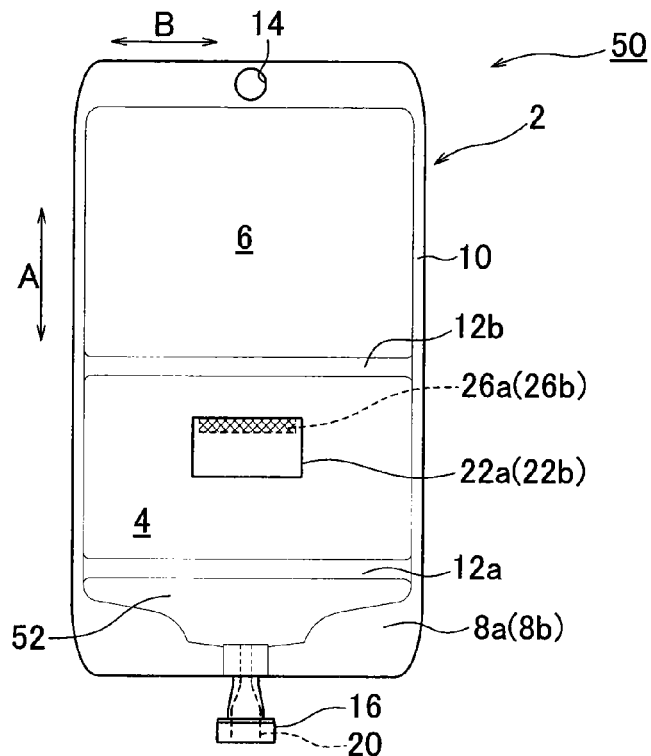
FIG. 7 is a front view of a third-embodiment drug bag according to the present invention.
Figure 8:
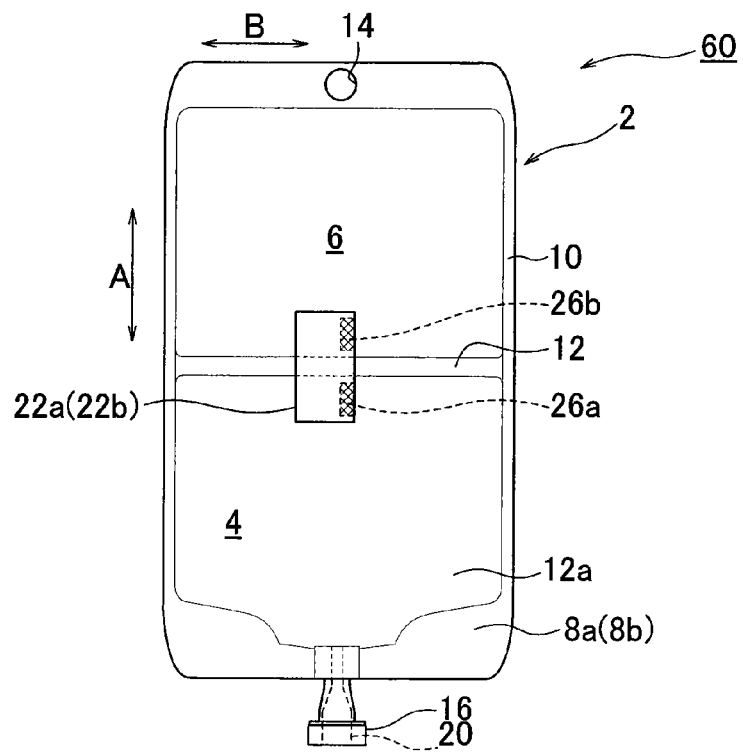
FIG. 8 is a front view of a fourth-embodiment drug bag according to the present invention.
Figure 9:
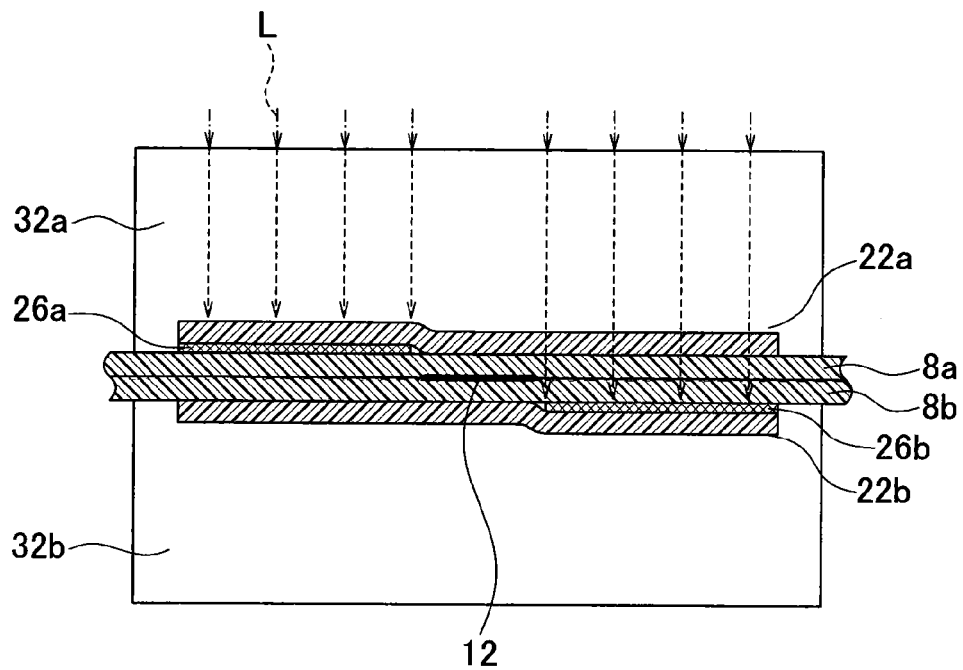
FIG. 9 is a view for explaining a process of fusion-bonding plastic films for handles to plastic films for a bag body in the drug bag shown in FIG. 8.
Figure 10:
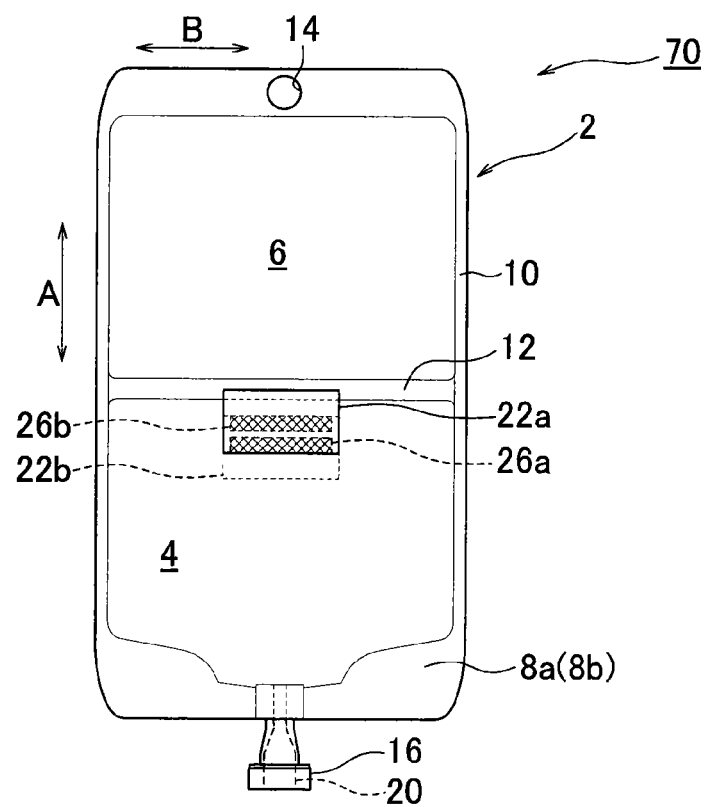
FIG. 10 is a front view of a fifth-embodiment drug bag according to the present invention.
Figure 11:
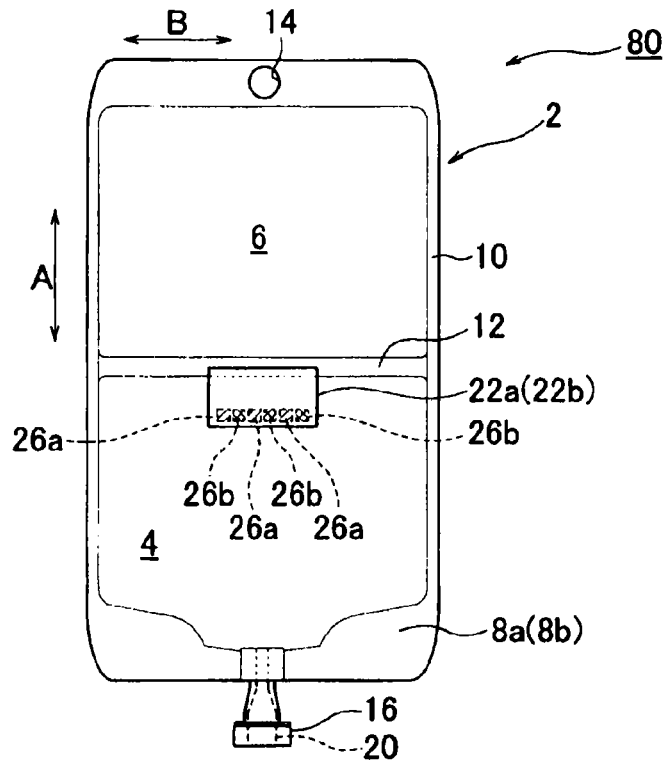
FIG. 11 is a front view of a sixth-embodiment drug bag according to the present invention.
Figure 12:
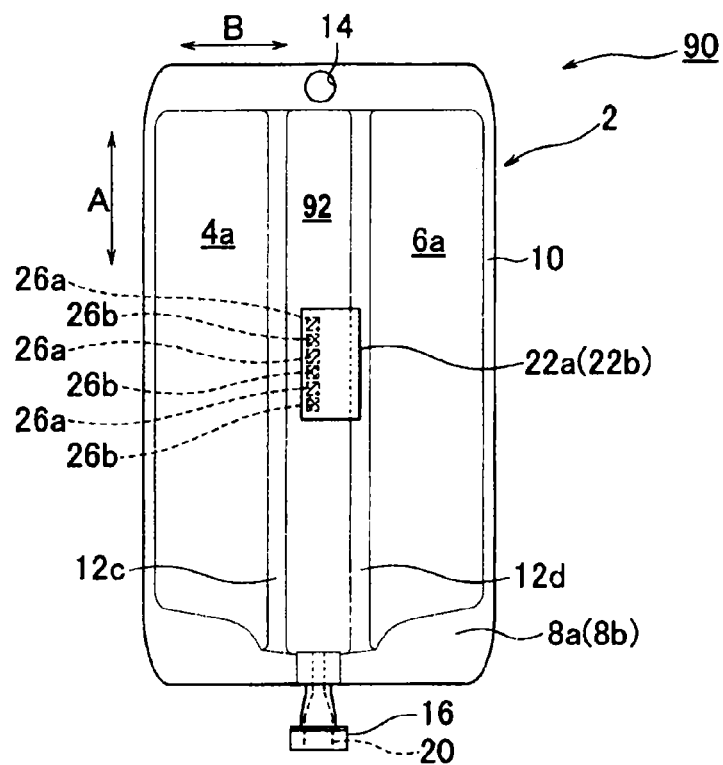
FIG. 12 is a front view of a seventh-embodiment drug bag according to the present invention.
Figure 13:
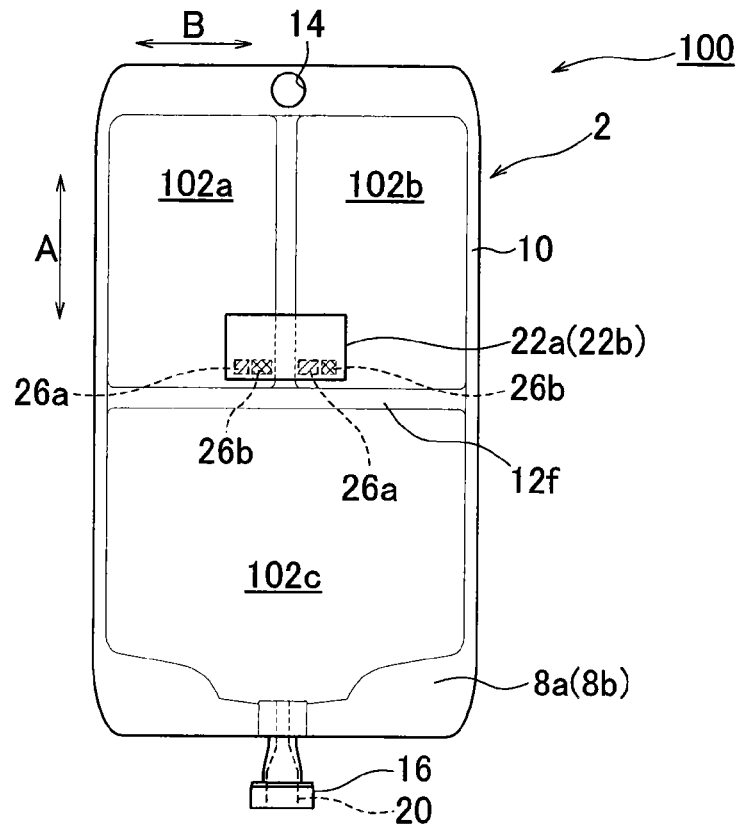
FIG. 13 is a front view of an eighth-embodiment drug bag according to the present invention.
Figure 14:
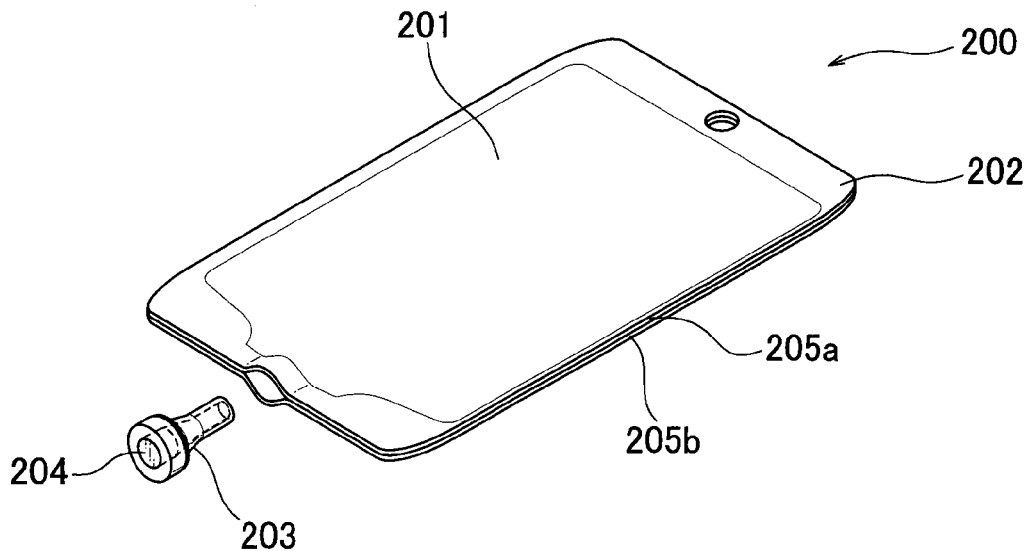
FIG. 14 is a schematic exploded perspective view of a conventional drug bag.
Figure 15:
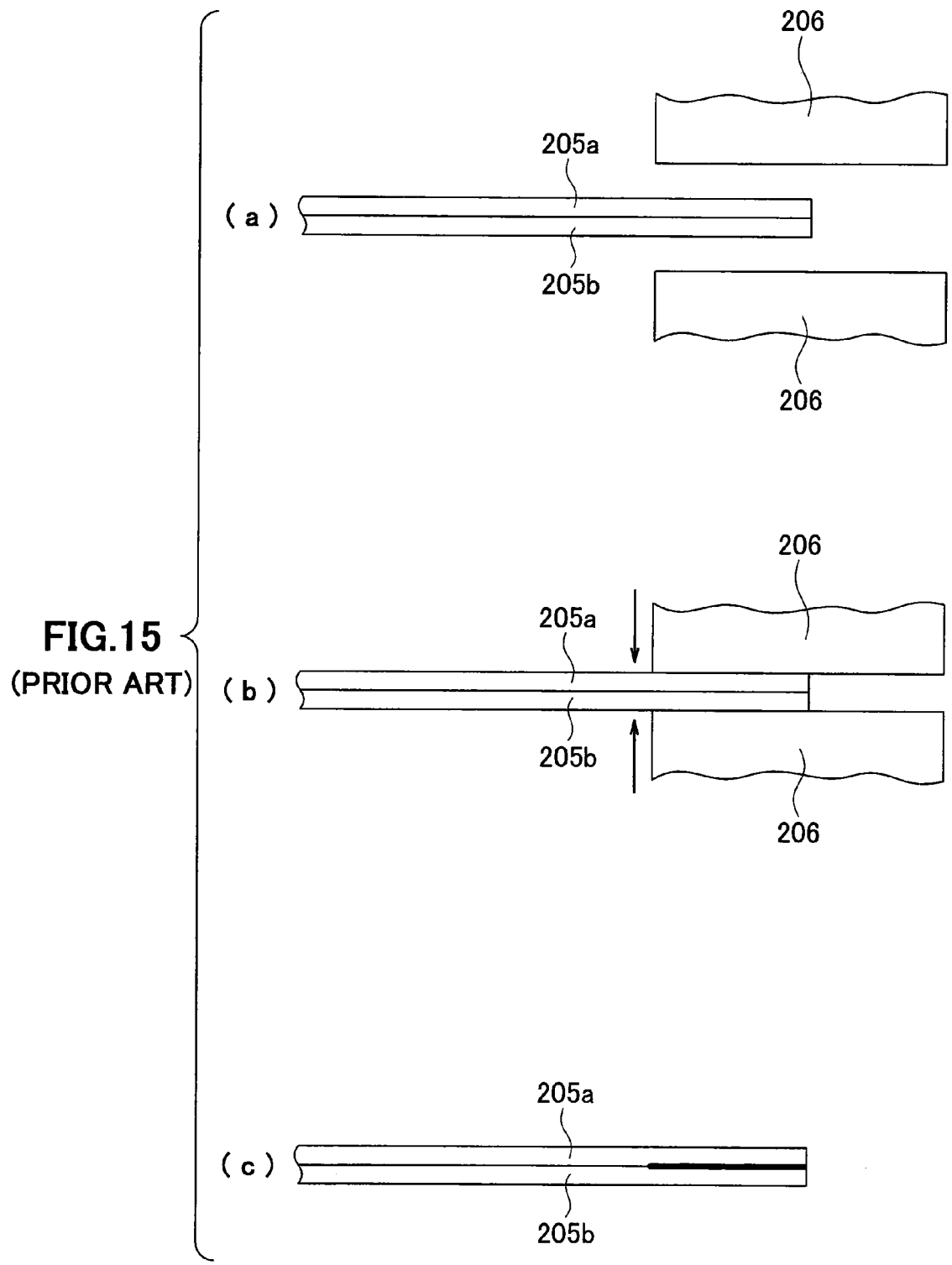
FIG. 15 is a view for explaining a fusion-bonding process at peripheral portions of plastic films.
Figure 16:
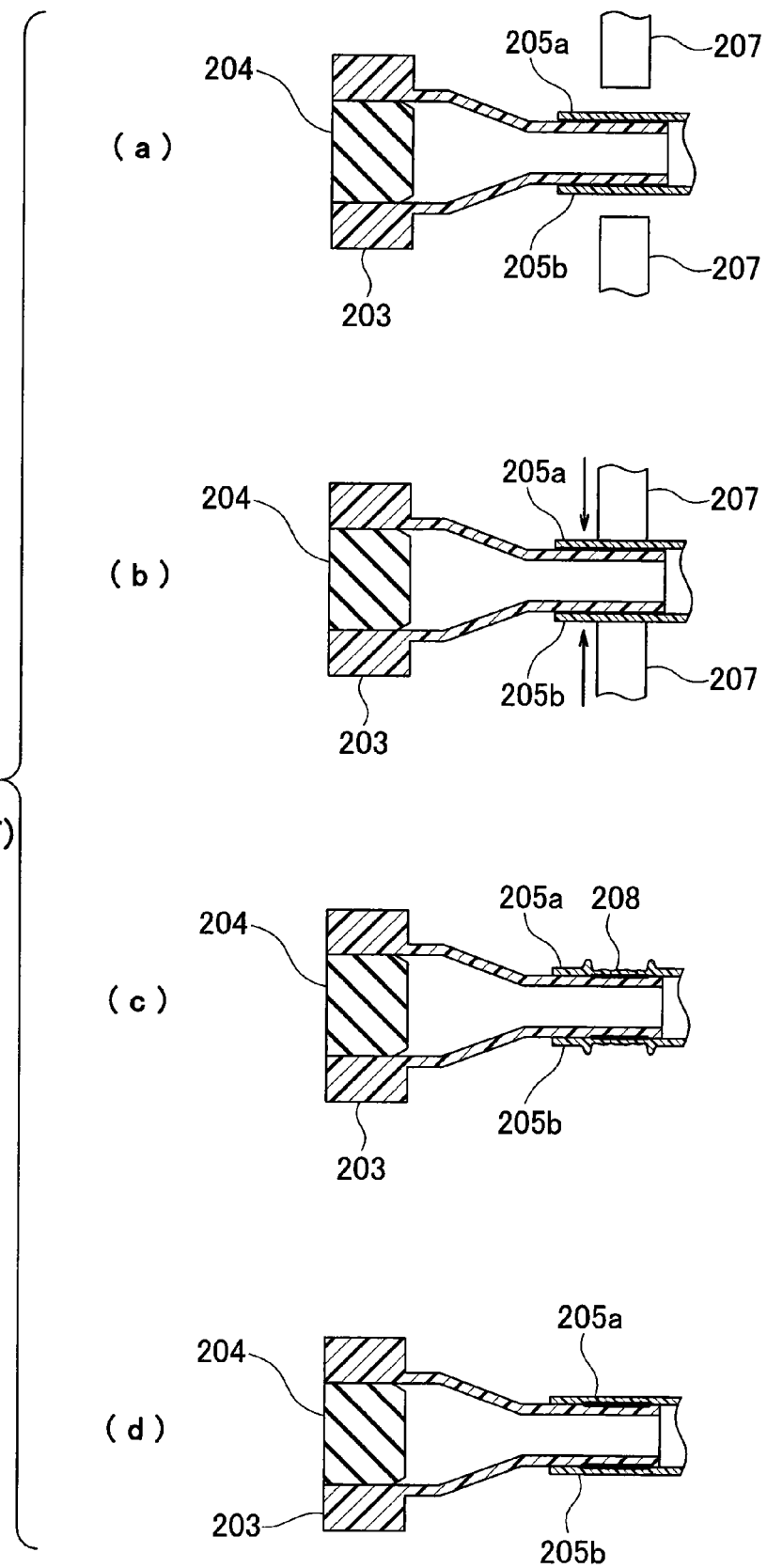
FIG. 16 is a view for explaining a fusion-bonding process between plastic films and a port member.
Figure 17:
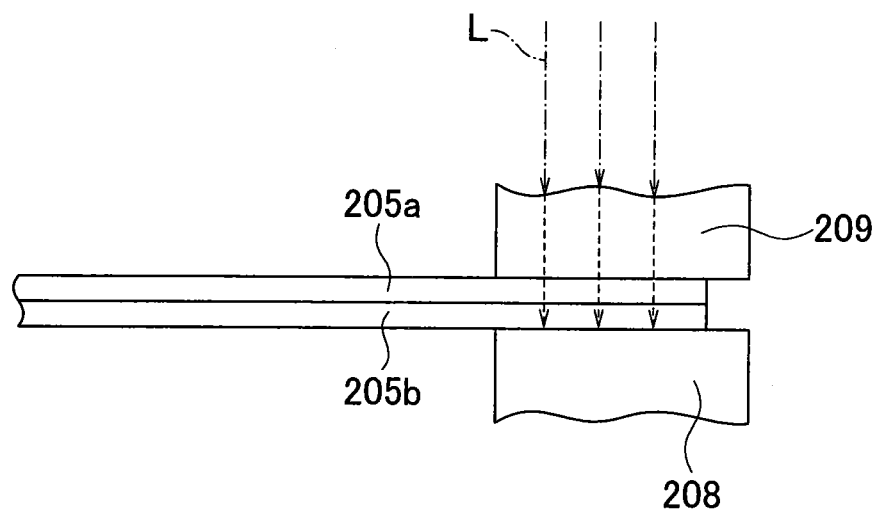
FIG. 17 is a schematic view for explaining a fusion-bonding process in prior art.

What is claimed is:

1. A process of manufacturing a drug bag, comprising:
sealing a front-side plastic film and a back-side plastic film such that a drug bag body having a plurality of compartments is formed, the plurality of compartments comprising a first compartment and a second compartment separated by a weak seal portion;
placing a portion of a port member between the front-side plastic film and the back-side plastic film;
placing a plastic film for a handle on a front surface of the front-side plastic film;
disposing a heat generation element on a front surface of the plastic film for the handle;
pressing a press member toward the heat generation element, the plastic film for the handle and the front-side plastic film;
irradiating infrared laser to the heat generation element through the press member during the pressing such that the heat generation element generates heat by absorbing infrared laser transmitted through the press member; and
fusion-bonding the plastic film for the handle of the front-side plastic film,
wherein the port member is placed such that one of the compartments communicates with outside of the drug bag body through the port member, the weak seal portion is unsealable by pulling the plastic film for the handle away from the front-side plastic film of the drug bag body, the weak seal portion includes a first weak seal portion near the port member and a second weak seal portion far from the port member, and
the heat generation element is disposed at equal distances from the first weak seal portion and the second weak seal portion.

2. The process according to claim 1, wherein the infrared laser has a wavelength belonging to a wavelength band of 700-1200 nm.

3. A process of manufacturing a drug bag, comprising:
sealing a front-side plastic film and a back-side plastic film such that a drug bag body having a plurality of compartments is formed, the plurality of compartments comprising a first compartment and a second compartment separated by a weak seal portion;
placing a portion of a port member between the front-side plastic film and the back-side plastic film;
placing a plastic film for a handle on a front surface of the front-side plastic film;
disposing a heat generation element on a front surface of the plastic film for the handle;
pressing a press member toward the heat generation element, the plastic film for the handle and the front-side plastic film;
irradiating infrared laser to the heat generation element through the press member during the pressing such that the heat generation element generates heat by absorbing infrared laser transmitted through the press member; and
fusion-bonding the plastic film for the handle of the front-side plastic film,
wherein the port member is placed such that one of the compartments communicates with outside of the drug bag body through the port member, the weak seal portion is unsealable by pulling the plastic film for the handle away from the front-side plastic film of the drug bag body, the weak seal portion includes a first weak seal portion near the port member and a second weak seal portion far from the port member, and
the heat generation element is disposed nearer the second weak seal portion than the first weak seal portion.

4. The process according to claim 3, wherein the infrared laser has a wavelength belonging to a wavelength band of 700-1200 nm.

5. A process of manufacturing a drug bag, comprising:
sealing a front-side plastic film and a back-side plastic film such that a drug bag body having a plurality of compartments is formed, the plurality of compartments comprising a first compartment and a second compartment separated by a weak seal portion;
placing a plastic film for a first handle on a front surface of the front-side plastic film;
disposing a heat generation element on a surface of the plastic film for the first handle;
placing a plastic film for a second handle on a back surface of the back-side plastic film;
pressing a press member toward the heat generation element, the plastic film for the first handle and the front-side plastic film;
irradiating infrared laser to the heat generation element through the press member during the pressing such that the heat generation element generates heat by absorbing infrared laser transmitted through the press member; and
fusion-bonding the plastic film for the first handle of the front-side plastic film, wherein,
the weak seal portion is unsealable by pulling the plastic film for the first handle away from the front-side plastic film of the drug bag body
the disposing of the heat generation element comprises positioning a first heat generation element adjacent to the plastic film for the first handle and a second heat generation element adjacent to the plastic film for the second handle without overlapping each other in a laser irradiation direction,
the infrared laser is irradiated from a front side of the drug bag body to the first heat generation element through the press member and to the second heat generation element through the front-side plastic film and the back-side plastic film, and
the infrared laser is transmitted through the front-side plastic film and the back-side plastic film.

6. The process according to claim 5, wherein the first heat generation element is formed in a plurality, the second heat generation element is formed in a plurality, and the first heat generation elements and the second heat generation elements are alternately disposed in a line form.

7. The process according to claim 6, wherein the infrared laser has a wavelength belonging to a wavelength band of 700-1200 nm.

8. The process according to claim 5, wherein the infrared laser has a wavelength belonging to a wavelength band of 700-1200 nm.

* * * * *